United States Patent [19]

D'Antonio

[11] Patent Number: 5,080,648

[45] Date of Patent: Jan. 14, 1992

[54] HYPODERMIC FLUID DISPENSER

[76] Inventor: Nicholas F. D'Antonio, 7695 Admiral Dr., Liverpool, N.Y. 13090

[21] Appl. No.: 336,636

[22] Filed: Apr. 7, 1989

Related U.S. Application Data

[63] Continuation of Ser. No. 59,620, Jun. 8, 1987, abandoned.

[51] Int. Cl.$^5$ .............................................. A61M 11/00
[52] U.S. Cl. ........................................ 604/72; 604/71; 604/135
[58] Field of Search ............... 604/68, 71, 72, 67, 604/134, 135, 151-155, 192, 198, 191, 212, 214, 263, 416; 128/DIG. 1

[56] References Cited

U.S. PATENT DOCUMENTS

| | | | |
|---|---|---|---|
| 1,880,354 | 7/1931 | Mueller | 604/134 |
| 2,675,802 | 4/1954 | Hein | 604/68 |
| 2,762,369 | 9/1956 | Venditty | 604/68 |
| 2,800,903 | 7/1957 | Smoot | 604/68 |
| 3,134,380 | 5/1964 | Armao | 604/198 |
| 3,136,313 | 6/1964 | Enstrom et al. | 604/139 |
| 3,138,157 | 6/1964 | Ziherl et al. | 604/71 |
| 3,262,449 | 7/1966 | Pannier et al. | |
| 3,419,007 | 12/1968 | Love | 604/72 |
| 3,490,451 | 1/1970 | Yahner | |
| 3,526,225 | 9/1970 | Isobe | |
| 3,557,784 | 1/1971 | Shields | 604/68 |
| 3,649,299 | 3/1972 | Sholl | |
| 3,985,535 | 10/1976 | Bennett et al. | |
| 4,014,206 | 3/1977 | Taylor | 604/122 |
| 4,059,107 | 11/1977 | Iriguchi et al. | |
| 4,103,684 | 8/1978 | Ismach | |
| 4,396,384 | 8/1983 | Dettbarn et al. | |
| 4,400,171 | 8/1983 | Dettbarn et al. | 604/68 |
| 4,410,323 | 10/1983 | Hodosh et al. | 604/212 |
| 4,413,991 | 11/1983 | Schmitz et al. | 604/191 |
| 4,416,663 | 11/1983 | Hall | 604/198 |
| 4,424,057 | 1/1984 | House | 604/88 |
| 4,518,385 | 5/1985 | Lindmayer et al. | |
| 4,529,401 | 7/1985 | Leslie et al. | 128/DIG. 1 |
| 4,552,277 | 11/1985 | Richardson et al. | 604/411 |
| 4,592,742 | 6/1986 | Landau | 604/71 |
| 4,623,332 | 11/1986 | Lindmayer et al. | 604/68 |
| 4,668,220 | 5/1987 | Hawrylenko | 604/155 |
| 4,725,267 | 2/1988 | Vailcancourt | 604/198 |
| 4,753,638 | 6/1988 | Peters | 604/212 |

FOREIGN PATENT DOCUMENTS 0087314  8/1959  Denmark ........................... 604/134

OTHER PUBLICATIONS

Mode of Operation of the Compressor in a Jet Injector, Meditsinskaya Tekhniko, vol. 11, No. 1 pp. 23-27, Jan.-Feb. 1977.

Comparative Evaluation of Three Jet Injectors for Mass Immunization, Canadian Journal of Public Health, vol. 68, pp. 513-516, Nov.-Dec., 1977.

Efficacy of an Adsorbed Trivalent Split Influenza Vaccine Administered by Intradermal Route, Arch. Roum. Path. Exp. Microbiol., T. 40, No. 1 pp. 67-70, Jan.-Mar., 1981.

Primary Examiner—Stephen C. Pellegrino
Assistant Examiner—Ralph A. Lewis
Attorney, Agent, or Firm—D. Peter Hochberg; Mark Kusner; Louis J. Weisz

[57] ABSTRACT

Needle and high velocity jet hypodermic injectors employ a tubular liquid chamber, a suitable output port i.e., a needle or a jet port, and corresponding means for applying pressure to collapse the liquid chamber.

The needle injector includes a needle sheath which automatically covers the needle after use and inhibits reuse of the needle. The jet injector electronically controls and monitors the system parameters of operation to assure successful injection results.

39 Claims, 8 Drawing Sheets

HYPODERMIC FLUID DISPENSER

This is a continuation of application Ser. No. 059,620 filed June 8, 1987 now abandoned.

TECHNICAL FIELD

This invention relates to apparatus for the hypodermic injection of fluids.

BACKGROUND OF THE INVENTION

Hypodermic fluid dispensers fall into two broad categories, namely: needle hypodermic dispensers and jet injectors. Jet injectors are particularly useful in immunization programs which involve the delivery of a non-living virus; and needle injectors are useful in the delivery of a non-living virus and of medications.

In general, jet inoculation, as compared to needle inoculation, is less traumatic, presents a lower risk of cross contamination, requires less operator training, and allows a higher number of procedures per unit of time.

Although both needle hypodermic injectors and high pressure jet injectors have been widely used, the presently known devices have serious disadvantages. The problems associated with needle injectors in the spread of AIDS (Acquired Immune Deficiency Syndrome) alone is sufficient motivation to avoid proliferation of today's needle systems. People cannot be relied upon to dispose of needle injectors in accordance with instructions and good practice; and an element of the population are tempted to reuse needles without knowledge of or regard for safe practices.

Jet injectors generally avoid the above referenced problems associated with needle injectors; however, the presently available injectors are expensive; prone to failure; too bulky to transport conveniently; and are generally inconvenient to use.

DISCLOSURE OF THE INVENTION

In accordance with the present invention a hypodermic fluid dispenser comprises: a collapsible tubular body forming a fluid chamber, a liquid outflow port for communication with the liquid chamber, and means for applying Pressure to one end of the body to discharge liquid through the output port.

Advantageously, my invention is applicable to both needle injectors and high pressure jet hypodermic injectors.

THE DRAWING

The invention is illustrated in the accompanying drawing in which:

FIG. 8 illustrates the details for the serum cartridge of the FIG. 7 jet injector.

DETAILED DESCRIPTION

Figure 1:
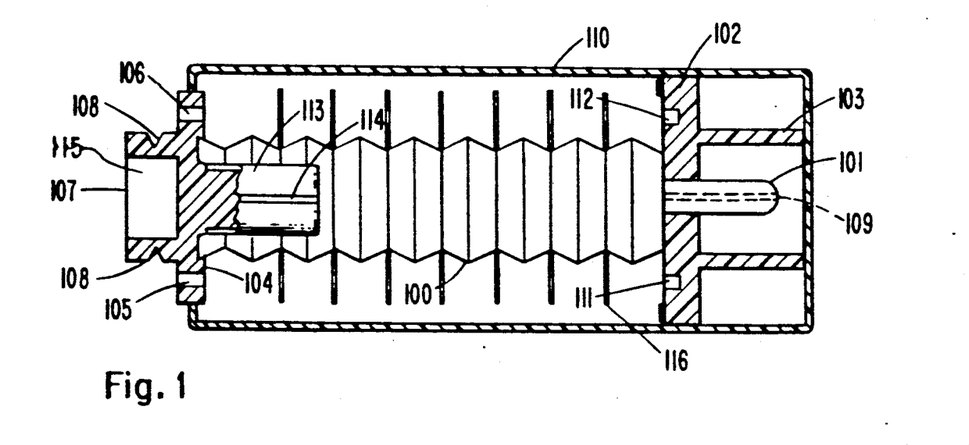
FIGS. 1 and 1 illustrate two multiple inoculation jet injectors in accordance with my invention.

FIG. 1 illustrates a liquid filled jet injector stored in a protective cover 110. The jet injector of FIG. 1 comprises: a liquid filled bellows 100; a front plate 102 which comprises: a pair of guide rod recesses 111 and 112, a set of thin washers 116 which have an inner diameter slightly larger than the minor diameter of bellows 100, a pair of holes in each of the washers 116 that are aligned with the guide rod recesses 111 and 112 and with the openings 105 and 106; a spacing guard ring 103, with an interrupted pattern to prevent sliding between the dispenser and the skin; a disposable and replaceable exit nozzle 101 with an output port 109; a ram 113 with a groove 114; and a back plate 104. Guard ring 103 can advantageously have the features shown in FIGS. 1B. An interrupted pattern at the end of ring 103 in FIG. 1B prevents sliding between the dispensers and the skin of the person being injected. The back plate comprises openings 105 and 106, aligned with holes 117 in washers 116, which accept a pair of guide rods when the injector cartridge is installed in the system of FIGS. 2a and 2b; and a ring 115 which forms the recess 107 for receiving a drive spring 227 of the system of FIG. 2a. The injector of FIG. 1 may be a disposable injector or a permanent reusable injector and the output port may be removable and replaceable or a permanent part of the bellows. In either case, device economy is improved by fabricating a molded output port having the flow orifice formed by first inserting a preformed metal, or other sufficiently sturdy member, whose size and shape i.e., length, diameter and flow path angulation are chosen to provide laminar flow. Some of the other possible methods for forming the orifice include laser boring, water jet cutting and electron beam cutting.

Figure 2:
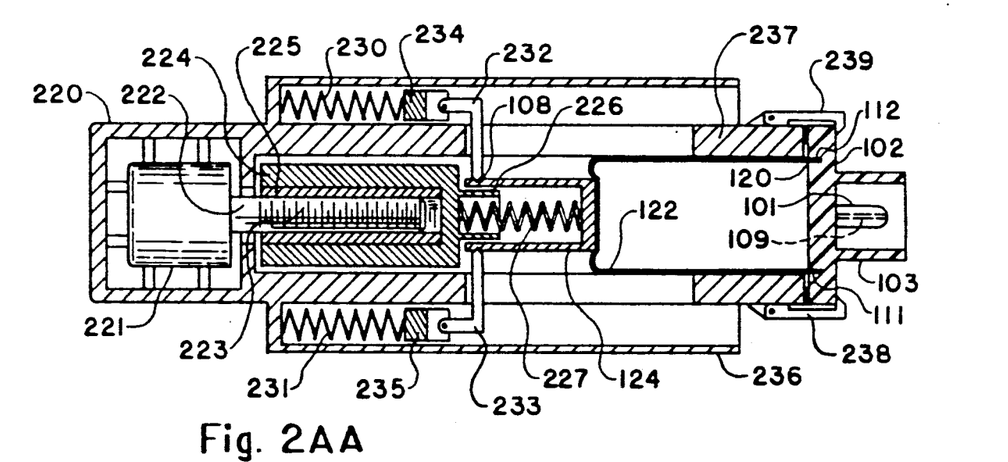
Figure 2A:
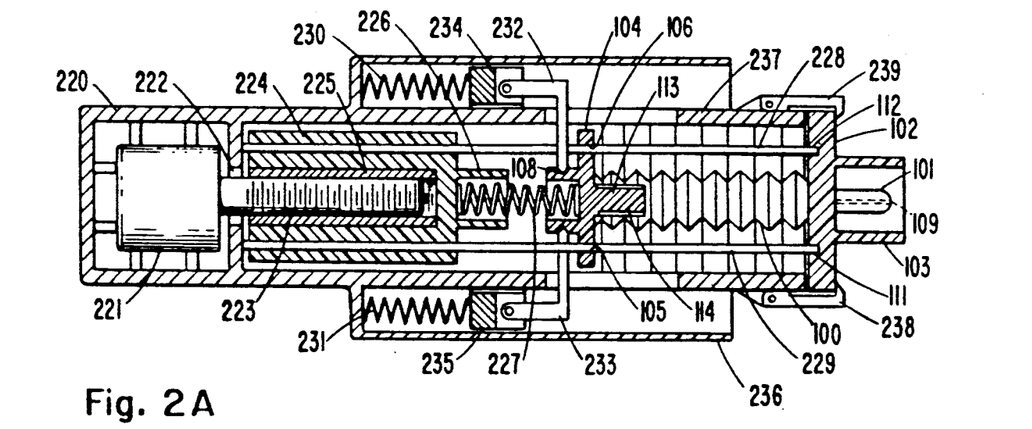
FIGS. 2a and 2aa illustrate jet injector systems with fresh injectors of FIGS. 1 and 1A installed therein.

FIG. 2a is a cross section representation of an illustrative embodiment of a hypodermic jet injector system with a fresh jet injector of FIG. 1 installed therein. The system of FIG. 2 in general comprises: a housing 220; the control, monitoring and display arrangements of FIGS. 3 and 4 (not shown in FIG. 2a); a battery operated drive motor 221; a motor output shaft 222 with a threaded portion 223; a loading ram 224 with internal threads 225 which mate with the threads 223; an energy storage spring 227; a reluctance transducer shield 226 to be described with respect to FIG. 3 later herein; a pair of guide rods 228 and 229 that serve to align and support the bellows 100; retaining latches 238 and 239; and a trigger mechanism which comprises the detents 232 and 233, the follower springs 230 and 231 and the follower blocks 234 and 235. The mechanism for releasing the detents 232 and 233 is not shown in FIG. 2 and any suitable mechanical linkage which effects the simultaneous lifting of the detents 232 and 233 is satisfactory.

Figure 1A:
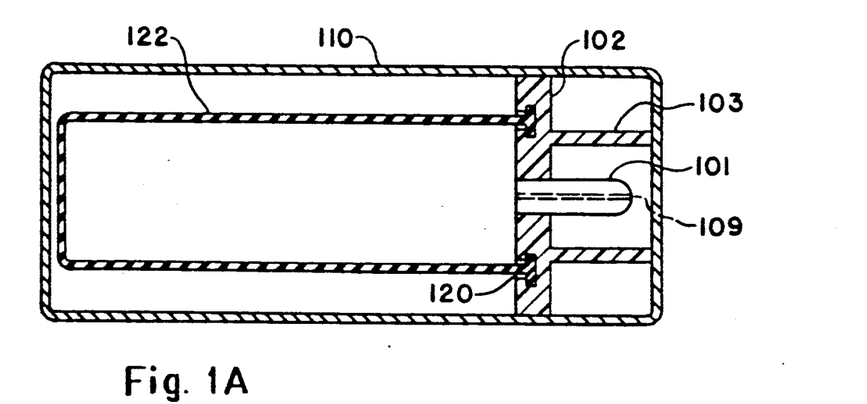
Figure 1B:
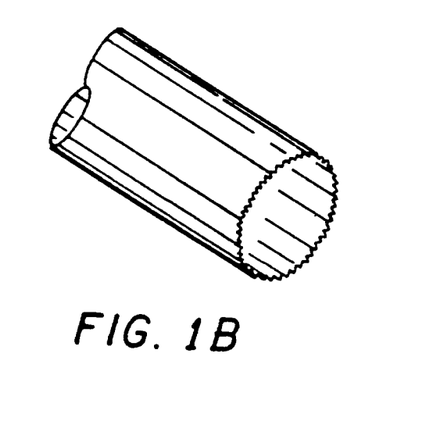
FIG. 1B is a partial pictorial view of a modified body guard.
Figure 2B:
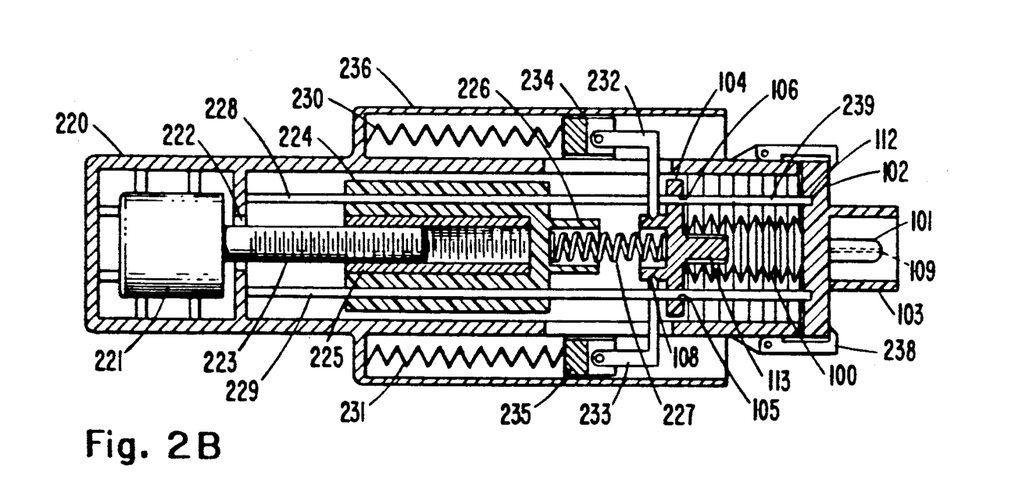
FIGS. 2b and 2bb illustrate the jet injector systems of FIGS. 2a and 2aa with the injectors partially expended.

An alternate embodiment of the injector of FIGS. 1, 2a and 2b is illustrated in FIGS. 1a, 2aa, and 2bb. In the alternate embodiment, the liquid filled bellows 100 is replaced by a collapsible liquid filled "hat" diaphragm type structure. Detents 111 and 112 of FIG. 1 are replaced in FIG. 1a by slot 120 for mounting and firmly securing hat structure 122 to the front plate 102.

FIG. 2aa is a cross section representation of the injector system with a fresh injector installed therein. When the diaphragm 122 is inserted in the now conformal housing 220, a slight initial collapse of 122 occurs to facilitate chamber venting and to assure an effective inner folding action as the multiple injections follow. The conformal shape of housing 220 constrains fluid chamber 122 and thus prevents undesired outward expansion under the influence o the injection pressure when the spring 227 is released. Back plate 124 is configured to assure that the detents 232 and 233 do not interfere with fluid chamber 122 as it progressively folds inside its outside diameter (FIG. 2bb) with each additional injection.

While the following discussion is specific to the embodiment of FIGS. 1,2a and 2b, the discussion applies equally to the alternate embodiment of FIGS. 1a, 2aa and 2bb.

Figure 3:
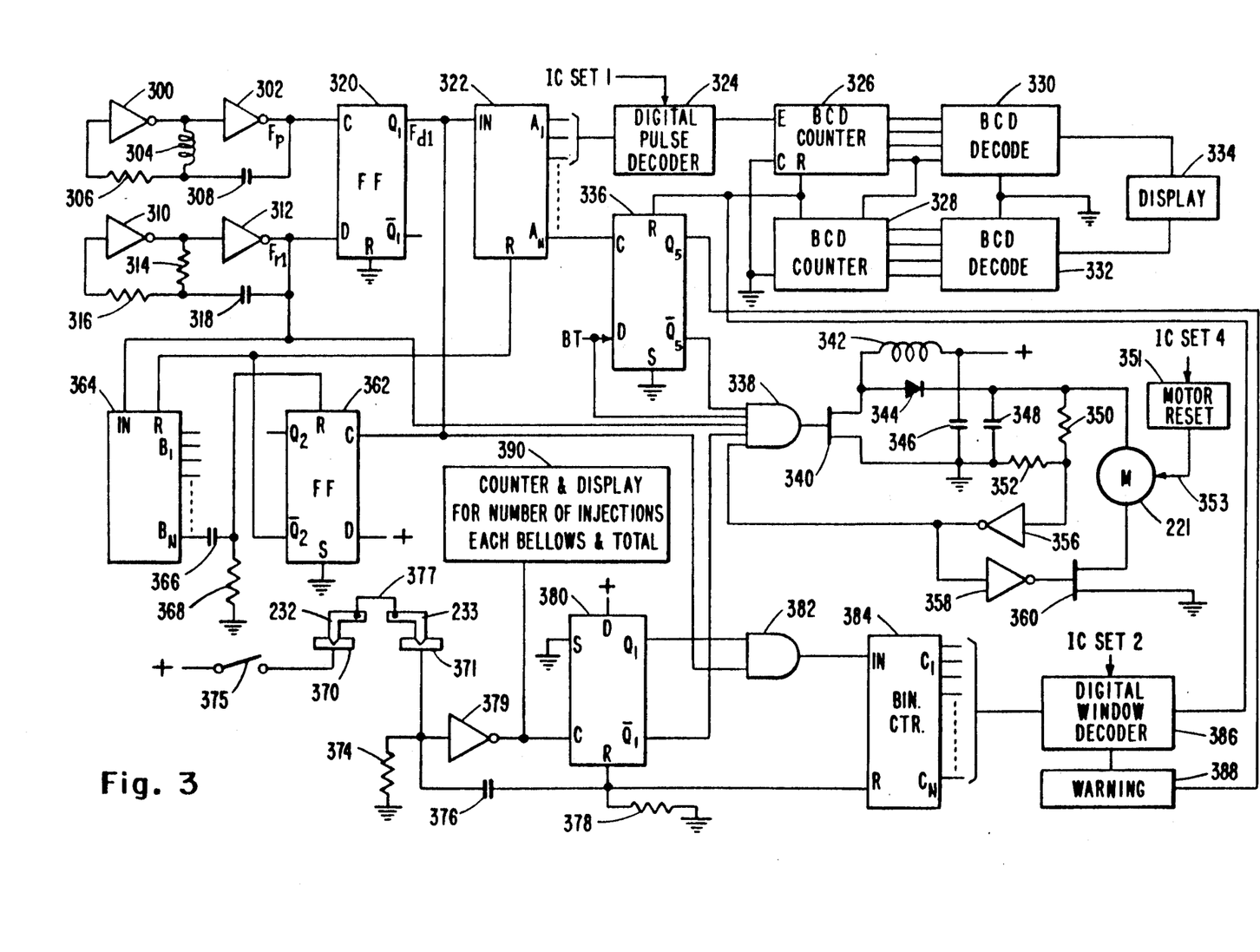
FIG. 3 and FIG. 4 are a schematic representation of the control and monitoring circuitry of the jet injector system of FIG. 2.
Figure 4:
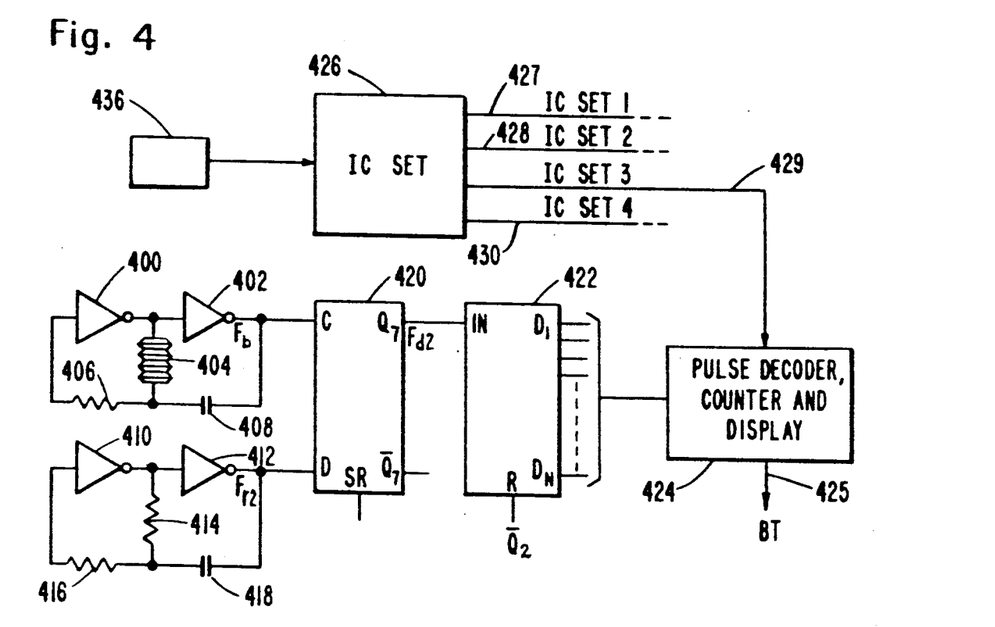

Prior to the time that a fresh jet injector of FIG. 1 is installed in the system of FIG. 2, a manually operated reset switch 436 of FIG. 4 is operated to enable the IC Set circuit 426 of FIG. 4 to establish initial system conditions. Output signals of the circuit 426 serve to: enable motor reset 351 of FIG. 3 to draw the loading ram 224 back into the initial position illustrated in FIG. 2a; and to initialize the digital pulse decoder 324, the digital window decoder 386 and the pulse decoder, counter, and display 424. Alternatively, the ram 224 can be manually returned to the initial position at the time that a fresh bellows is installed.

The functions of the pulse decoder 324, the window decoder 386 and the pulse decoder counter and display 424 will be apparent from the description of FIGS. 3 and 4 which appears later herein. After the system is thus conditioned, a fresh jet injector is removed from the protective cover 110 and inserted into the housing 220 as illustrated in FIG. 2a. To install the jet injector, the guide rods 228 and 229 are inserted into the openings 105 and 106 in the back plate 104, through the openings 117 in the washers 116, and the injector is moved into the housing 220 until the front face of the front plate 102 is clamped by the latches 238 and 239. As the jet injector is moved into the housing 220, the detents 232 and 233 engage the notches 108 in the back plate 104 and follow the motion of the back plate as it is moved to the left in FIG. 2a. The follower blocks 234 and 235 follow the motion of the detents 232 and 233 to the left and thus compress the follower coil springs 230 and 231. Further, when a fresh injector is in position as illustrated in FIG. 2a, the energy storage spring 227 enters the recess 107 in the back side of the back plate 104. The system of FIG. 2a is in condition for an operator to perform a series of inoculations.

Under operator control, the system of FIGS. 2a, 3 and 4 selectively provides power to the motor 221 to advance the ram 224 to the right in FIG. 2a and thus compress the coil spring 227. As described later herein, the circuitry of FIG. 3 monitors the degree of compression of the spring 227 and removes power from the motor when the compression reaches a target value. The target value is either a default value established by the manufacturer or a value established by an operator on the basis of experience. After the spring has been compressed to the target value, the guard 103 is held perpendicular to and against the skin at a suitable site of a subject to be injected. The outer ring surface of guard 103 may have a tooth like pattern to reduce the possibility of the ring sliding along the skin during the course of an injection. If the ring does slide during the injection the subject may receive a "jet cut" rather than a jet inoculation. The operator initiates injection by depressing a trigger, which as indicated earlier herein is not shown in the drawing. Depression of the trigger simultaneously releases the detents 232 and 233 from the recesses 108 in the back plate 104. The energy stored in the spring 227 is released and the back plate 104 is rapidly driven to partially collapse the bellows 100. As the bellows is collapsed, a desired amount of fluid is driven through the output port 109 in the projection 101. Advantageously, the use of a compressed spring as a source of energy provides a high initial pressure which reduces as the bellows 100 collapses. The size and the length of the port 109 and the pressure profile supplied by the compressed spring projects the fluid with a desired pressure profile which assures hypodermic injection of the fluid to the desired depth. The diameter and the length of the port 109 are chosen to assure laminar flow of the liquid from the chamber to the output tip. As the bellows collapse, guide washers 116 move together and prevent the bellows from bending under the influence of the high initial force of the injection.

As explained earlier herein, when a fresh injector is inserted into the housing 220, the follower springs 230 and 231 are compressed. Therefore, after the trigger is released, the follower blocks 234 and 235 and the detents 232 and 233 are driven to the right in FIG. 2a until the detents again engage the corresponding recesses 108 in the back plate 104. The follower blocks 234 and 235 may be connected to a small dashpot if a delay in this action is desired. The system of FIG. 2a is then again ready for the operator to initiate another injection.

Because the wall of the bellows 100 has a finite thickness, a fully collapsed bellows has a substantial length. The length of the ram 113 approximates the length of the collapsed bellows. Without the ram 113, valuable fluid is left in a fully collapsed bellows. The groove 114 in the ram 113 prevents the trapping of fluid in the portions of the bellows which surround the ram 113.

The above description is a general outline of the inoculation process without detailed reference to the control, monitoring and display apparatus of FIGS. 3 and 4. While it is my intent to provide safe, low cost and convenient to use hypodermic injectors, I also provide measures of electronic monitoring and control not found in known jet injectors.

Figure 6:
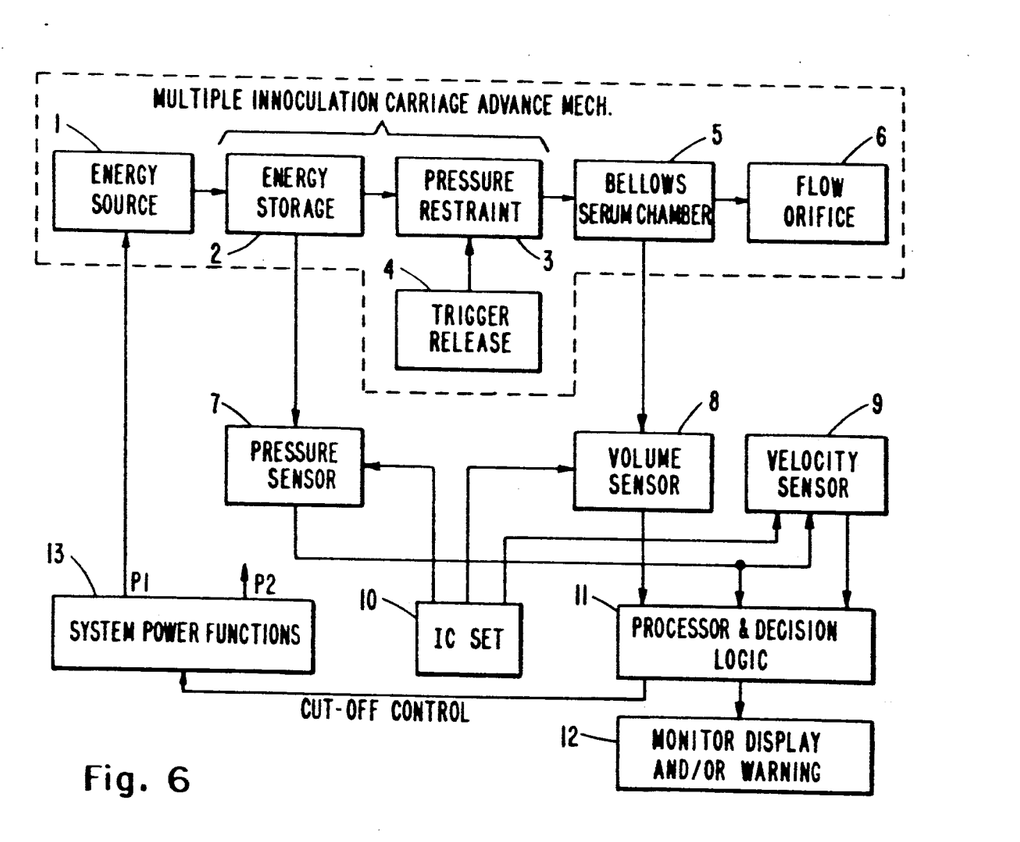
FIG. 6 is a block diagram overview of a multiple inoculation jet injector system in accordance with my invention.

FIG. 6 provides a block diagram functional overview of a hypodermic jet injector system in accordance with my invention. The dotted line of FIG. 6 provides a logical division between the mechanical portions of the injector system and the electronic monitoring and control portions of the system.

The functional boxes 1 through 6 of FIG. 6 correspond to elements of the illustrative embodiment of FIGS. 2a and 2b as follows:

| FIG. 6 | FIG. 2a |
|---|---|
| Energy Source 1 | Motor 221 |
| Energy Storage 2 | Spring 227 |
| Pressure restraint 3 | Detents 232 & 233 |
| Trigger release 4 | Not shown in drawing |
| Bellows serum chamber 5 | Jet injector of FIG. 1 including Bellows 100 |

| FIG. 6 | FIG. 2a |
| --- | --- |
| Flow orifice 6 | Output port 109 |

Although the illustrative embodiment of FIG. 2a employs a battery operated geared down motor 221 to compress the coil spring 227, this requirement can be fulfilled by a variety of manual arrangements utilizing gears or other means of mechanical advantage. While the spring is preferred for storing the energy, the blocks 1 and 2 of FIG. 6 could be replaced by other arrangements e.g., a powerful solenoid. The critical requirement of the blocks 1 and 2 is that the bellows 100 receives enough force for a sufficient period of time to assure an effective inoculation.

The monitoring functions of FIG. 6 inform an operator when the device is ready to perform an injection i.e., all system parameters are within acceptable limits of performance. A warning is issued when performance is not within limits and the system is disabled in the event of a malfunction.

The pressure sensor 7 of FIG. 6 monitors the status of the energy storage device 2 and compares the magnitude of the stored energy to a target magnitude. When the magnitude of the energy stored reaches the target value, the storage of energy is terminated. The target value may be a default value established by the manufacturer or a value established by the operator on the basis of experience with different subjects e.g., adults, children, animals which may be better served with different pressures. The target pressure value is one of the "initial conditions" which an operator may set by controls in the IC Set function 10 of FIG. 6.

The volume sensor 8 provides assurance that a correct amount of liquid is used in each injection.

The velocity sensor 9 of FIG. 6 determines the time required for the stored energy to decay to equilibrium after an injection. The decay time is a measure of output port performance. If the output port is partially clogged, the pressure decays too slowly; and if the output port is worn or too large the pressure will decay too rapidly. If a failure is detected, a warning will be issued to the operator and the system is disabled until corrective action is taken.

The IC Set 10 of FIG. 6 permits an operator to select initial condition values for the pressure sensor 7, the volume sensor 8 and the velocity sensor 9.

The processor and decision logic 11 issues control signals to the system power control 13 and status signals to the monitor display and warning unit 12.

In addition to the control and monitoring function described above herein, the circuit arrangements of FIG. 4 maintain a record of the number of injections completed.

The implementation of the system functions by the arrangements of FIGS. 3 and 4 will be understood from the following description.

Digital inverters 310 and 312, resistors 314 and 316, and capacitor 318 are configured to form a reference frequency oscillator. The operating frequency $F_{r1}$ is determined by the time constant of the resistor 314 and the capacitor 318.

Digital inverters 300 and 302, capacitor 308, and variable sensing inductance 304 in FIG. 3 form a variable frequency reluctance transducer oscillator which has an operating frequency $F_p$. The operating frequency of the oscillator varies as a function of the value of the inductance 304. The coil 304, which is not shown in FIG. 2a is mounted at the center of recess 107 and inside the energy storage spring 227 and is partially covered by the reluctance shield 226 of FIG. 2a. A change in the relative position of the coil 304 and the shield 226 as the spring 227 is compressed changes the inductance of the coil 304. Accordingly, the frequency of the oscillator, which is determined by the time constant of the inductance 304 and the capacitor 308, is determined by the degree of compression of the spring 227. A reluctance transducer oscillator with a sensing inductance as described above is known from my U.S. patent application Ser. No. 607,654 filed May 7, 1984.

Flip flop 320 is configured as a frequency mixer which provides a digital output signal which has a pulse rate $F_{d1}$ which is the difference between the reference pulse rate $F_{r1}$ and the oscillator frequency $F_p$. In the absence of pressure on the spring 227, the frequencies $F_{r1}$ and $F_p$ are equal and the pulse rate $F_{d1}$ at the "1" output of flip flop 320 is zero.

In the illustrative embodiment of FIG. 3, the motor 221 is driven by a series of high energy, relatively high voltage pulses. The output of AND gate 338 controls the generation of the motor drive pulses. The inputs to the AND gate 338 comprise: the "0" output of the flip flop 336 which remains high until the target value of spring compression is reached; the BT conductor from pulse decoder 424; the "0" output of the flip flop 380 which is high except when the trigger is activated to initiate an injection; the output of the inverter 356 which is high until the charge on capacitor 348 reaches a critical value., and the output conductor of the reference oscillator. When enabled, the output signal of AND gate 338 turns the FET 340 on and off at the rate $F_{r1}$ of the reference oscillator. When the transistor 340 is on, current will flow from positive potential through inductance 342 and the transistor 340, to ground. When the transistor 340 is subsequently turned off, the energy stored in the magnetic field of coil 342 will discharge through the path which is comprised of diode 344 and capacitor 348. The resistors 350 and 352 are of relatively high value; therefore, very little energy is lost in the path to ground through those two resistors. The magnitude of the voltage generated by the collapse of the magnetic field of coil 342 is very high and is dictated by the rate of collapse of the field. The rate of collapse is determined by the impedance of the discharge path. The diode 344 prevents reverse flow of current due to the build up of voltage on the capacitor 348. Capacitor 346 is a stabilizing capacitor which provides an extra measure of current for the coil 342 during the ON state of transistor 340. When the charge on capacitor 348 reaches a predetermined value the output of the threshold detector 356 will go low and gate 338 is disabled. The predetermined value represents a charge large enough to advance the motor 221. When the output of detector 356 goes low, the output of inverter 358 goes high to enable transistor 360 to provide a path for discharging the capacitor 348 through the winding of motor 221. When the charge on the capacitor falls below the threshold value of detector 356, the output of detector 356 goes high to enable gate 340 to initiate another cycle of charging capacitor 348; and the output of inverter 358 goes low to disable transistor 360. Charging cycles will continue until flip flop 336 is set to the "1" state which indicates that the energy stored in spring 227 has reached the target value. In the drawing.

the output labeled $Q_5$ is the "1" output of the flip flop 336 and the complement output is termed the "0" output herein.

Flip flop 336 is controlled by the An output conductor of counter 322, by an output signal of the digital window decoder 386, and by the BT conductor. The flip flop 336 is set to the "1" state when the $A_n$ output of the counter 322 goes high if the BT conductor is high; and is reset by the output conductor of the decoder 386. Counter 322, in turn, is controlled by the $F_{dl}$ signal at the output of flip flop 320 and by the output of flip flop 362. Flip flop 362 is set by a $F_{dl}$ signal at the output of flip flop 320 and reset by a $B_n$ output signal of counter 364. Counter 364 defines a period of time in terms of pulses of the reference frequency $F_{r1}$ and counter 322 counts the difference frequency pulses $F_{d1}$. Since counter 364 and counter 322 are reset at the same time by an output signal of flip flop 362, counter 364 provides a measurement window of time which runs from reset time to the next reset time. The $A_n$ output conductor will remain low until the deformation of the spring 227 reaches the target value. When the counter 322 reaches the $A_n$ count within the measurement time window, flip flop 336 is set and gate 338 is disabled. At the same time, the "1" output of flip flop 336 is transmitted to the warning function 388 to indicate that the device is ready for an injection procedure. Flip flop 336 can be set only if the BT input to the D terminal of that flip flop is high. As will be explained with respect to FIG. 4, the BT conductor will be high if the bellows test is satisfactory. The digital code which is stored in counter 322 during a measurement time interval corresponds to the instant deformation of the energy storage spring 227. The digital pulse decoder 324, in response to the digital code in counter 322, generates input signals for the BCD counters 326,328. For example, if the deformation of the spring which is equivalent to one pound of force on the spring provides ten cycles of differential frequency $F_{dl}$, decoder 324 will convert the code in counter 322 to a single pulse for BCD counters 326,328. With a count of one in the counters 326,328, the BCD decoders 330,332 provide signals to the display 334 to display the value, one pound. Any number can be displayed with appropriate decoding by pulse decoder 324. By virtue of the display 334, the operator knows that the appropriate level of energy is stored in the spring 227 and that an injection may be initiated. The flip flop 336 remains set until an injection has been successfully completed. If the velocity test fails, a warning in 388 will issue and flip flop 336 will not be reset. Accordingly, remedial action must be taken before preparation for another injection can be started.

The power on switch 375 in the lower left portion of FIG. 3, connects positive battery potential to the input of inverter 379 through the contact segments 370 and 371, detents 232 and 233, and link 377. The contact segments 370 and 371 lie in the recesses 108 on the back plate 104 shown in FIG. 1 and in FIG. 2. When the trigger is operated, the detents 232 and 233 are disconnected from the contact segments 370 and 371; and, because the input is referenced to ground through resistor 374, the output of inverter 379 goes high. A high signal from the output of inverter 379 increments a counter in 390 to display the number of injections completed from the current bellows; and causes the "D" type flip flop 380 to be set to the "1" state. Consequently the "0" output of flip flop 380 goes low which disables AND gate 338. The high signal on the "1" output of flip flop 380 enables AND gate 382 to pass $F_{dl}$ difference frequency signals to the input of counter 384. As explained earlier herein the difference frequency will reduce to zero when the spring 227 comes to equilibrium after an injection. The count which is accumulated in the counter 384 is thus representative of the time required for the bellows to be partially collapsed. The window decoder 386 evaluates the count in the counter 384 on the basis of the expected values established by IC 2. If the count is larger than the expected limits, it is probable that the output port is plugged and if the count is smaller than the expected limits it is probable that the output port is enlarged beyond acceptable limits. In either event, a warning signal is displayed by the warning indicator 388 and the flip flop 336 will not be reset until remedial action is taken. If the count in counter 384 is within limits, an output signal of digital decoder 386 will reset flip flop 336 and the BCD counters 326 and 328. When that occurs, the cycle to drive the motor to load energy into the spring 227 will again start. The time required for the bellows to partially collapse is short compared to the time required for the detents 232 and 233 to again settle in the recesses 108 and reconnect positive potential to the input of inverter 379. This time relationship is positively assured if a dashpot is employed to slow the return as suggested earlier herein. When the positive potential reappears at the input of inverter 379, capacitor 376 and resistor 378 which are configured as a high pass filter, produce a reset pulse to flip flop 380 and counter 384 in preparation for the next injection. In the event that a very large volume injection is to be performed, the time required to inject the fluid may exceed the time for the detents 232 and 233 to settle in recess 108. In that case the illustrative high pass reset circuitry can be replaced with circuitry with appropriate delay.

FIG. 4 provides an arrangement for testing the integrity of the liquid filled bellows 404. Inverters 400 and 402 are configured as an oscillator in which the output frequency $F_b$ is determined by the impedance across the entire bellows 404. Inverters 410 and 412 are configured as a fixed frequency oscillator having a frequency $F_{r2}$; and flip flop 420 is connected as a frequency mixer for the signals $F_{r2}$ and $F_b$. In the configuration of FIG. 4, the collapsing bellows behaves as a variable resistance; therefore, the frequency of the mixer output signal $F_{d2}$ is minimum when the bellows is full. As the bellows collapses, the impedance decreases and the differential signal $F_{d2}$ increases. The counter 422 accumulates the $F_{d2}$ signals during a measurement time interval defined by the "0" output conductor of flip flop 362 of FIG. 3; and pulse decoder and display 424 displays bellows status information. The use of the time period provided by the Dn count is for purposes of illustration. In the event that a different time period is desired, additional counter outputs and flip flops are provided. The arrangements of 424 evaluate the interval count in counter 422 on the basis of the IC set 3 information which defines a range or window of acceptable values. If the count falls within the range of acceptable values, a high BT signal will be generated and flip flop is set on occurrence of the next succeeding An signal from counter 322. However, if the serum within the bellows has excessive voids, clots or an incorrect consistency for some reason or another, the $F_b$ frequency will fall outside the acceptable range and the count in 422 will fall outside the preselected window of performance.

It should be noted that fluid may be used as a dielectric material in an alternative embodiment in which a variable capacitance determines the frequency $F_b$. In that embodiment the variable bellows is located at the position of the capacitor 408 and a fixed resistor placed at the position 404 in FIG. 4. In this case, the two ends of the bellows form the capacitor plates and the serum fluid is the dielectric material. As the length of the bellows decreases, the capacitance increases and the frequency $F_b$ decreases.

Figure 5A:
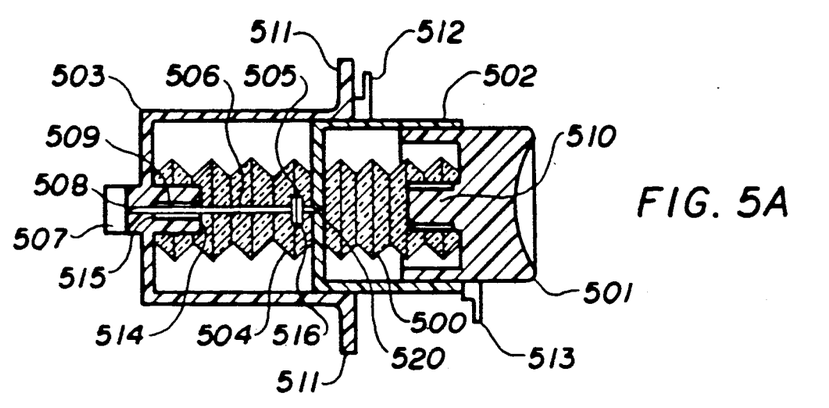
FIGS. 5a through 5d illustrate a needle hypodermic injector in accordance with my invention in a sequence of stages which occur in use of the injector.

FIGS. 5a to 5d show a needle type hypodermic injector in accordance with my invention in various stages in the use of the injector. The injector of FIG. 5a comprises a bellows 500 sealed with end cap and ram 510; a front housing 503, a rear housing 502; a pressure piston 501; a needle output port 508 with a flange 511; a bellows shaped needle sheath 504; and removable cap 507. FIG. 5a illustrates a fresh injector prior to use. As in the injector embodiment of FIGS. 1 and 2, the support guide rings 116 of those figures may be employed in the embodiment of FIGS. 5a to 5d. The bellows 500 may contain a liquid serum or a lyophilized (freeze dried) vaccine. In the latter case a liquid which is stored in the sheath bellows 504 is driven into the bellows 500 as the needle is exposed as described below herein. The bellows 500, the rear housing 502 and the front housing 503 all may be fabricated of clear plastic material so that the operator can observe whether or not blood is drawn into the bellows 500 when the pressure piston is slightly withdrawn.

Figures 5B, 5C, 5E:
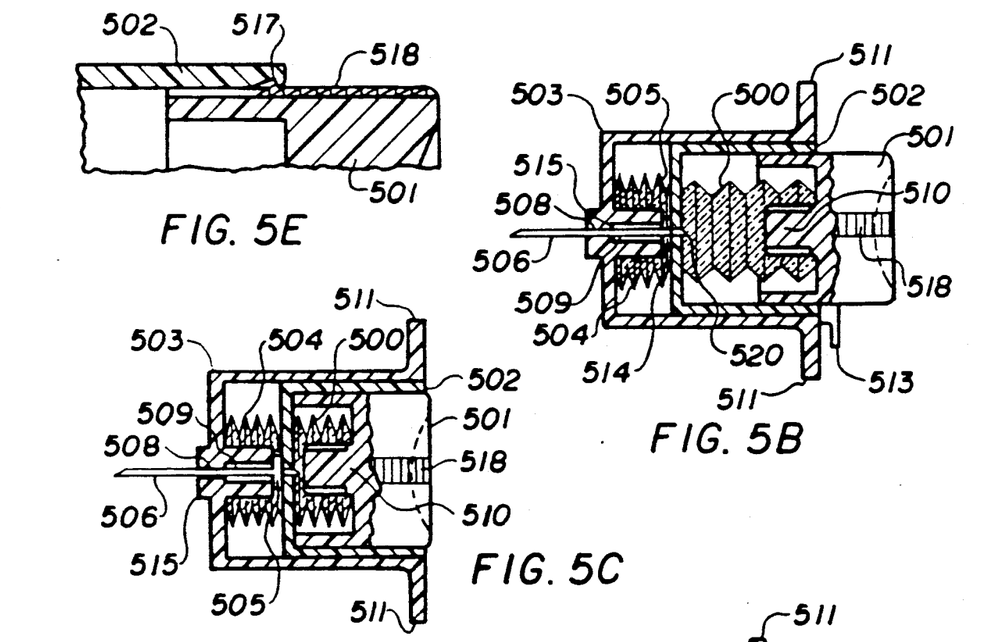

The break away seal 512 and the cap 507 are removed to permit the operator to expose the needle 506. The need to remove the cap 507 may be eliminated if the cap 507 is made of a self sealing material e.g., pure latex rubber. The needle is exposed by applying pressure on the flange 511 and the pressure piston 501 to draw them together. Typically, the thumb is placed on the pressure piston 501 and index finger and the adjacent finger are placed on the flange 511. The resistance of the sheath bellows 504 is sufficient to cause the bellows to expand after use; however, the resistance of the bellows 504 is small compared to the force required to compress the liquid bellows 500 to eject the liquid through the needle output port. Therefore as pressure is applied between the flange 511 and the pressure piston 501 the sheath bellows will begin to collapse and needle exposure will begin. As the sheath bellows is collapsed the right hand side 520 of needle 506 will puncture the membrane separating sheath bellows 504 and serum bellows 500. As compression continues, the liquid residing in sheath bellows 504 is forced into serum bellows 500 to form the fluid state of the desired serum. Ultimately, needle flange 505 will engage the surface 514 therein, after removal of breakaway seal 513, continued pressure will force the serum in 500 to be expelled through the exit port of needle 506, said serum being unable to reenter 504 because it has collapsed to zero internal volume. A foam ring 516 positioned on the right side of flange 505 serves as a cushion to prevent flange 505 from opening the membrane to a greater extent than that of puncture point 520. The membrane in 500 also can be made of self-sealing latex diaphragm material which will tend to hold the needle in place after the injection is completed and the sheath is again extended to cover the needle. The first intermediate state of the injector is illustrated in FIG. 5b.

In the cases where the serum is stored in bellows 500 in a liquid state. the bellows 504 can be replaced with a simple coil spring. However, if as suggested earlier herein, the vaccine is stored in the lyophilized state, the fluid required to turn the vaccine to the liquid state is stored in the bellows 504. In this latter case, the liquid in bellows 504 is forced into bellows 500 through a hole in the membrane of the bellows 500 which is breached when the bellows 504 is first compressed to begin exposure of needle 506.

After the needle is inserted into the injection site, pressure is applied between the break away seal 513 is removed and pressure piston 501 and the flange 511 to collapse the liquid bellows 500 and eject fluid through the output port into the injection site. The state of the injector after depletion of the injection fluid is illustrated in FIG. 5c. As shown in FIG. 5e, a sawtooth pattern 518 on the outer surface of the pressure piston 501 and a single sawtooth 517 on the inner surface of the rear housing 502 permit the pressure piston 501 to be advanced into the member 502 and thus compress the bellows 500. However, the cooperation of 517 and 518 prohibits withdrawal of the piston 501 after engagement of 517 and 518. As an option, the end of the ram 510 is shaped to strike and crush the end 520 of the needle 506 when the bellows 500 is fully collapsed. This will further assure that the needle injector cannot be reused and will tend to retain the needle in engagement with the bellows 500 when the sheath bellows 504 and the sheath 503 are extended to cover the needle.

Figure 5D:
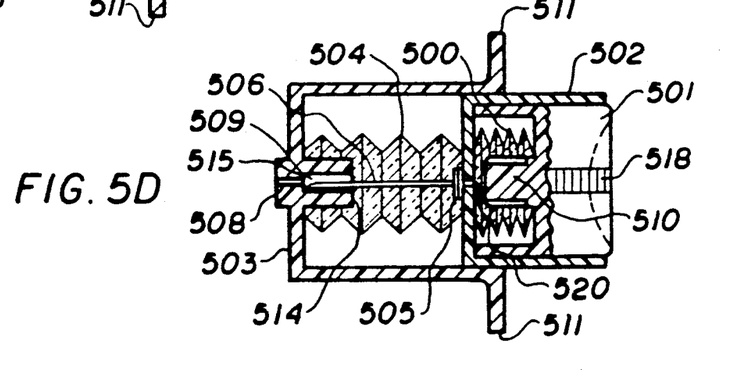

After the needle is removed from the subject and pressure between 501 and 511 is removed, the bellows 504 expands as shown in FIG. 5d. As seen in FIG. 5d, when the needle sheath bellows 504 extends to its full length, the needle 506 is withdrawn from the needle guide 508. This occurs because in preparation for the injection, end 520 of needle 506 penetrated the membrane to breach the serum chamber. Because the needle guide opening 508 is small compared to the trap opening 509, it is difficult if not impossible to again collapse the bellows 504 without the end of the needle 506 hitting the end wall 515 of the trap section 509. The tendency of the needle to hit the wall 515 can be enhanced by imparting a small bend in the needle 506 prior to initial installation into the guide opening 508.

Figure 7:
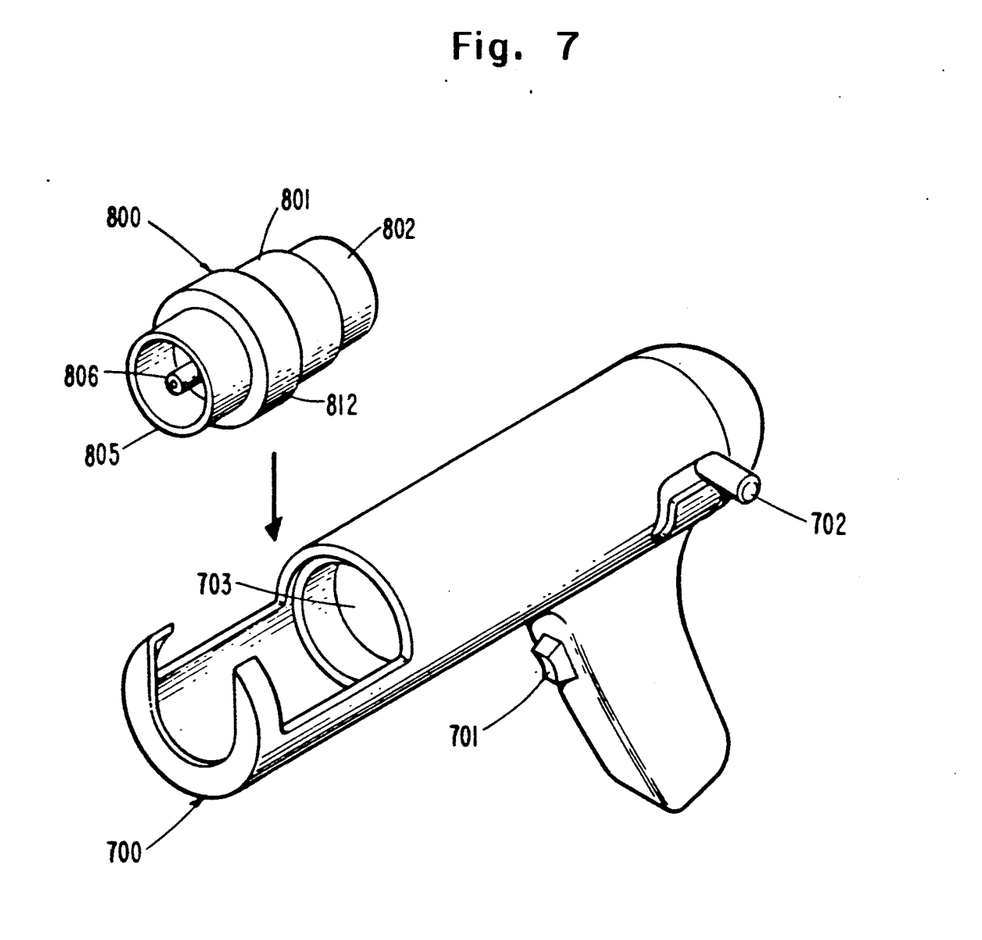
FIG. 7 is an alternative embodiment of a jet injector in accordance with my invention.
Figure 8A:
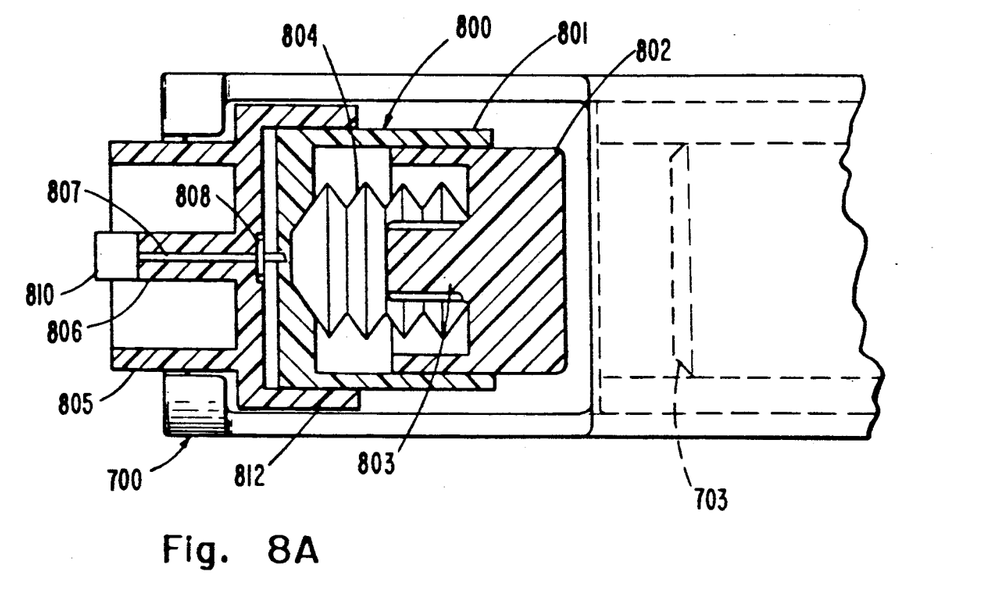
FIG. 8a shows the jet injector system illustrated in FIG. 7 with a fresh cartridge installed therein.
Figure 8B:
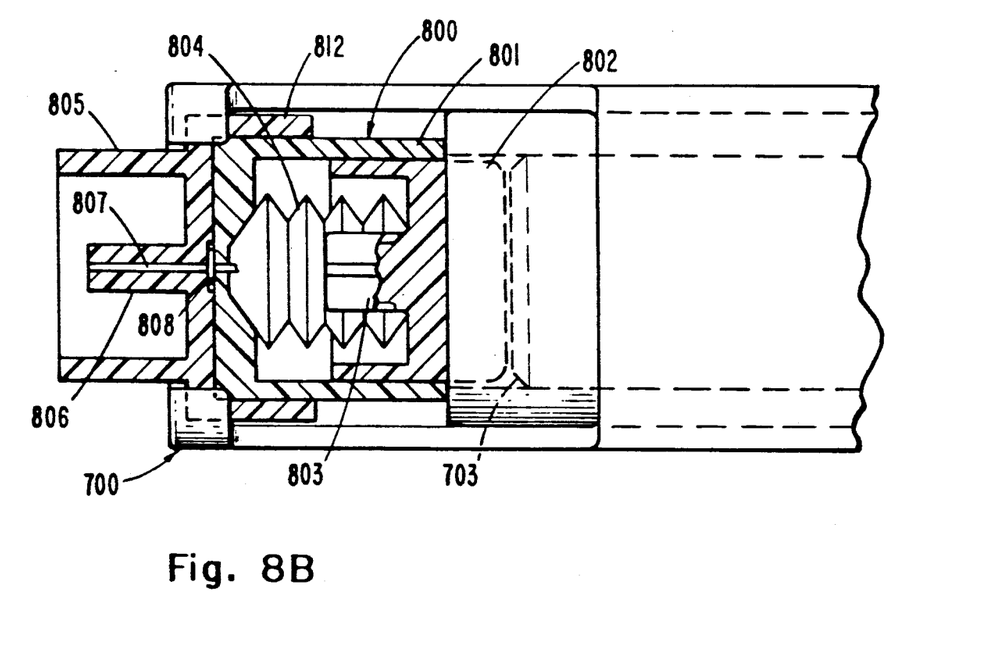
FIG. 8b shows the jet injector system of FIG. 7 in which the cartridge has been breached.

FIG. 7 shows an alternative embodiment of a jet injector system and a cartridge for that system. Details of the cartridge are shown in FIGS. 8a and 8b. The system of FIG. 7 can be proportioned to handle single shot or multiple shot cartridges. The lever 702 is drawn to the rear to permit a used cartridge to be removed and a fresh cartridge installed. After a fresh cartridge is installed, the lever 702 is moved forward, to the left in FIG. 7. The system of FIG. 7 can be modified to use a chamber for a number of cartridges which move serially into the system for use. Any suitable driving force can be utilized to drive the pressure piston forward to collapse the bellows 804 in the cartridge 800.

The cartridge of FIG. 8a comprises a sealed serum bellows 804 with a ram 803; a rear housing 801; a pressure piston 802; a front housing 812 which comprises a guard ring 5 805 and a jet output port 807 with a flange 808; and removable cap 810. FIG. 8a illustrates a fresh injector installed in the system of FIG. 7 prior to breaching the seal of the serum bellows 804.

FIG. 8b illustrates the arrangements of FIG. 8a after the lever 702 of FIG. 7 is moved forward to breach the seal of the bellows 804 and to bring the injector piston 703 in position to drive the pressure piston 802 forward to collapse the bellows 804.

The illustrative embodiments of my invention which are disclosed herein are but representative of my invention and many changes in form and function can be made without departing from the spirit and scope of my invention.

What is claimed is:

1. A hypodermic fluid dispenser for receiving a collapsible body forming a chamber for holding a fluid, said dispenser comprising:
   pressure application means for applying pressure to said body to at least partially collapse said body, to force fluid held in said chamber therefrom, said pressure application means including:
   repetitively charged storage means for storing electrical energy of relatively high value, said storage means being connectable to a primary source of electrical energy, the energy of said storage means being higher than the instantaneous energy available from said primary source;
   resilient means operatively connectable to said collapsible body received in said dispenser for expanding from a compressed state to collapse said body;
   motor means for compressing said resilient means;
   means for connecting said motor means to said resilient means; and
   a source of electrical pulses having relatively high energy and short duration, said source being energized by said repetitively charged storage means capacitor and transmitting relatively high energy, short duration pulses to energize said motor means.

2. The invention according to claim 1 wherein said resilient means is spring means.

3. The invention according to claim 1 wherein said motor means is repetitively operable to compress in increments said resilient means.

4. The invention according to claim 3 wherein said source of electrical pulses energizes said motor means repeatedly as said motor means is repetitively operable.

5. The invention according to claim 1 wherein said pressure application means applies pressure to said body to at least partially collapse said body to permit a partial flow of said fluid from said body, wherein a subsequent application of pressure to said body will permit a subsequent flow of fluid from the body.

6. The invention according to claim 1 and further including means for terminating said energizing pulses to said motor means when said collapse reaches a predetermined value.

7. A hypodermic fluid dispenser having a collapsible body, an outlet from said body, resilient means operatively connected to said body for deforming to at least partially collapse said body to force fluid from said outlet, said dispenser further comprising:
   monitoring means for monitoring the deformation of said resilient means, said monitoring means including a source of reference pulse signals having a first pulse rate, and a source of monitor pulse signals having a monitor pulse rate directly related to the magnitude of the deformation of said resilient means.

8. The combination of a hypodermic fluid dispenser and a collapsible body forming a chamber for holding a fluid received in said dispenser;
   said collapsible body comprising output means for discharging fluid from said body when said body is at least partially collapsed; and
   said dispenser comprising pressure application means for applying pressure to said body to at least partially collapse said body, to force fluid held in said chamber from said output means, said pressure application means including:
   repetitively charged storage means for storing electrical energy of relatively high value, said storage means being connectable to a primary source of electrical energy, the energy of said storage means being higher than the instantaneous energy available from said primary source;
   resilient means operatively connectable to said collapsible body for expanding from a compressed state to collapse said body;
   motor means for compressing said resilient means;
   means for connecting said motor means to said resilient means; and
   a source of electrical pulses having relatively high energy and short duration, said source being energized by said repetitively charged storage means and transmitting relatively high energy, short duration pulses to energize said motor means.

9. The invention according to claim 8 wherein guard means is provided near said output means for preventing contact between the patient's skin and said output means.

10. The invention according to claim 9 wherein said guard means comprises a guard ring, said guard ring being disposed generally on the opposite position of said collapsible body where said resilient means operatively connects to said collapsible body.

11. The invention according to claim 9 wherein said guard means has an interrupted pattern to prevent sliding between the dispenser and the skin.

12. A hypodermic fluid dispenser in accordance with claim 8 wherein the volume of said chamber when fully extended is N times the volume discharged by a single release of said energy, and wherein N is a whole number greater than 1.

13. A hypodermic fluid dispenser for receiving a collapsible body forming a chamber, said dispenser comprising:
   means for applying pressure to said body to discharge fluid from said chamber; and
   means for monitoring the performance of the dispenser comprising means for defining and storing time parameters of acceptable dispenser performance including a range of acceptable times for completion of an injection, timing means comprising means for measuring the time required to complete each injection and means for evaluating said measured time in terms of said range of acceptable times, means for evaluating dispenser performance in terms of said range of acceptable times, and means for displaying indications of dispenser performance.

14. A hypodermic fluid dispenser for receiving a collapsible body forming a chamber, said dispenser comprising:
   means for applying sufficient pressure to said body to discharge fluid from said chamber; and
   means for determining changes in electrical impedance of said fluid across said chamber in response to changes in the condition of said fluid.

15. The invention according to claim 14 wherein said condition is the impedance of said fluid, and wherein there if included means for comparing said impedance with the impedance of known values of said fluid to determine the amount of collapse of said body.

16. A multiple dose hypodermic fluid dispenser for receiving a collapsible body forming a chamber, said dispenser comprising:
   resilient means to store mechanical energy for subsequent application against said body during its collapse;
   motor means to deform said resilient means;
   means for connecting said motor means to said resilient means;
   said motor means applying mechanical pulses to energize said resilient means to collapse said body;
   a source of energizing pulses for said motor means;
   means for applying said energizing pulses to said motor means; and
   release means for releasing said resilient means to release the stored mechanical energy for producing a pressure injection pulse that causes at least a partial discharge of fluid contained in said body.

17. A hypodermic fluid dispenser according to claim 16 and further including:
   means for monitoring the deformation of said resilient means; and
   means for terminating said energizing pulses to said motor means when said deformation reaches a predetermined value.

18. A hypodermic fluid dispenser according to claim 17 and further including means for manually adjusting said predetermined value.

19. A hypodermic fluid dispenser in accordance with claim 17 wherein said means for monitoring the deformation of said resilient means comprises:
   a source of reference pulse signals having a first pulse rate;
   a source of monitor pulse signals directly related to the magnitude of deformation of said resilient means; and
   means for comparing said reference pulse signals and said monitor pulse signals.

20. A hypodermic fluid dispenser in accordance with claim 19 wherein said source of monitor pulse signals comprises a variable inductance for setting the pulse rate of said monitor pulse signals, and wherein said inductance is varied as a function of the deformation of said resilient means.

21. A hypodermic fluid dispenser in accordance with claim 16 wherein said dispenser includes means for displaying values which define the magnitude of deformation and the stored mechanical energy of said resilient means.

22. A multiple dose hypodermic fluid dispenser for receiving a collapsible tubular body forming a chamber, the volume of said chamber when fully extended being N times the volume discharged by a single release of energy, where N is a whole number greater than one, said dispenser comprising:
   resilient means to store mechanical energy;
   motor means to deform said resilient means;
   means for connecting said motor means to said resilient means;
   said motor means applying pulses to energize said resilient means to collapse said body;
   a source of energizing pulses for said motor means;
   means for applying said energizing pulses to said motor means; and
   release means for releasing said resilient means, to release said stored mechanical energy for producing a pressure injection pulse that causes at least a partial discharge of fluid contained in said body;
   means for counting said pressure injection pulses that cause said discharge of fluid; and
   means responsive to output signals of said counting means for displaying the number of said injection pulses.

23. A multiple dose hypodermic fluid dispenser for receiving a collapsible body forming a chamber, the volume of said chamber when fully extended being N times the volume discharged by a single release of said energy, where N is a whole number greater than one, said dispenser comprising:
   resilient means to store mechanical energy;
   motor means to deform said resilient means;
   means for connecting said motor means to said resilient means;
   said motor means applying pressure injection pulses to energize said resilient means to collapse said body;
   a source of energizing pulses for said motor means;
   means for applying said energizing pulses to said motor means;
   release means for releasing said resilient means, to release said stored mechanical energy for producing a pressure injection pulse that causes at least a partial discharge of fluid contained in said body; and
   means for monitoring the performance of said dispenser, said monitoring means including:
      timing means for defining and storing parameters of acceptable performance;
      means for evaluating dispenser performance in terms of said stored parameters; and
      means for displaying indications of dispenser performance.

24. A hypodermic fluid dispenser in accordance with claim 23 wherein said means for monitoring also includes means for inhibiting dispenser operation when dispenser performance falls outside an acceptable range of said stored parameters.

25. A hypodermic fluid dispenser in accordance with claim 24 wherein said stored parameters comprise a range of acceptable times for completion of an injection, and said monitoring means comprises means for measuring the time required to complete each injection, and means for evaluating said measured time in terms of said range of acceptable times.

26. A hypodermic fluid dispenser in accordance with claim 23 wherein said body is tubular and said stored parameters comprise a range of values which define an expected change in length of said tubular body during each said release of said energy, and said monitoring means further comprises means for measuring the changes in length of said tubular body during said releases of energy, and means for evaluating said measured changes in terms of said stored parameters.

27. A hypodermic fluid dispenser for receiving a collapsible body forming a chamber for holding said fluid, said dispenser comprising:
   pressure application means for applying pressure to said body to at least partially collapse said body, to force fluid held in said chamber therefrom, said pressure application means including:
      electrical energy storage means for storing electrical energy of relatively high value, said storage means being connectable to a primary source of electrical energy, the energy of said storage means being higher than the instantaneous energy of said primary source;

mechanical energy storage means for operative contact with said collapsible body for releasing energy from an activated state to collapse the received body;

motor means for activating said mechanical energy storage means;

means for connecting said motor means to said mechanical energy source means; and a source of electrical pulses having relatively high energy and short duration, said source being energized by said storage means and transmitting relatively high energy, short duration pulses to energize said motor means.

28. A multiple dose hypodermic fluid dispenser for receiving a collapsible body forming a chamber, said dispenser comprising:

mechanical energy storage means for operative contact with said collapsible body for releasing energy from an activated state to collapse a received body;

motor means to activate said storage means;

means for connecting said motor means to said mechanical energy storage means; and pulse means for applying pressure injection pulse to the received body, said pulse means including:

a source of energizing pulses for said motor means;

means for applying said energizing pulses to said motor means; and release means for releasing said mechanical energy storage means, said mechanical energy storage means being releasable from the activated state by said release means to release said stored mechanical energy for producing a pressure injection pulse that causes at least a partial discharge of fluid contained in the received body.

29. A hypodermic fluid dispenser comprising:

a collapsible body forming a chamber for holding a fluid, said body having an outlet;

pressure application means for applying pressure to said body to at least partially collapse said body, to force fluid held in said chamber therefrom, said pressure application means including:

repetitively charged storage means for storing electrical energy of relatively high value, said storage means being connectable to a primary source of electrical energy, the energy of said storage means being higher than the instantaneous energy available from said primary source;

resilient means operatively connected to said collapsible body received in said dispenser for expanding from a compressed state to collapse said body;

motor means for compressing said resilient means;

means for connecting said motor means to said resilient means; and a source of electrical pulses having relatively high energy and short duration, said source being energized by said repetitively charged storage means and transmitting relatively high energy, short duration pulses to energize said motor means.

30. Apparatus including a manually operated hypodermic fluid dispenser and a collapsible body forming an initially sealed chamber for holding a first serum ingredient, said apparatus comprising:

hypodermic needle means;

manual pressure means for manually applying pressure to said body for operating said dispenser;

a sheath for covering said needle means before and after use of said dispenser;

means for uncovering said needle means by said sheath in response to said manual pressure means applying pressure to said body;

second holding means for holding a second serum ingredient; said needle means being located in one of said serum ingredient holders positioned to penetrate the other serum ingredient holder, said penetration occurring to cause said first and second serum ingredients being brought together in response to pressure applied to said body.

31. Apparatus according to claim 30 and further including means within said dispenser to prevent said needle means from being operable after the needle means has been used.

32. A hypodermic fluid dispenser according to claim 31 wherein said needle means discharges the liquid serum as said manual pressure means operates the dispenser, said hypodermic needle means is isolated from said chamber, and said dispenser includes means for selectively bringing said hypodermic needle means into communication with said chamber.

33. A fluid dispenser according to claim 32 in which said said sheath is bellows-shaped.

34. A hypodermic fluid dispenser according to claim 31 and further comprising means for moving said sheath into communication with said body, and said manual pressure means is actuable to emit pressure to collapse said sheath to extend said needle means during operation of the dispenser.

35. The invention according to claim 34 wherein said means for applying pressure to deactuable to cause said sheath to expand, to retract said needle means into said sheath.

36. The invention according to claim 35 and further comprising means to prevent said needle means from being extended after said needle means has made an injection.

37. The invention according to claim 31 wherein said sheath is said second holding means.

38. A hypodermic fluid dispenser according to claim 31 wherein said sheath contains a liquid for converting non liquid serum to a liquid serum, and wherein during operation of the dispenser said needle means brings said sheath into communication said body to cause the liquid serum to enter said body to produce said liquid serum when said sheath is collapsed.

39. A hypodermic fluid dispenser in accordance with claim 31 wherein said dispenser is formed of a transparent material making the contents within the chamber visible.

* * * * *